(12) United States Patent
Mastny et al.

(10) Patent No.: US 6,190,919 B1
(45) Date of Patent: Feb. 20, 2001

(54) SYSTEM FOR CONTROLLING DEGLYCEROLIZATION OF RED BLOOD CELLS

(75) Inventors: Gary F. Mastny, San Diego; Hugh D. Copeland, Chula Vista; Andrew E. Patterson, San Diego, all of CA (US)

(73) Assignee: The United States of America as represented by the Secretary of the Navy, Washington, DC (US)

( * ) Notice: Under 35 U.S.C. 154(b), the term of this patent shall be extended for 0 days.

(21) Appl. No.: 09/295,875

(22) Filed: Apr. 21, 1999

(51) Int. Cl.[7] ................................................. G01N 33/48
(52) U.S. Cl. .......................... 436/63; 436/164; 436/165; 436/52; 422/58; 422/73; 422/81; 422/82.05; 356/39; 356/317; 356/318; 356/335; 356/336; 356/337
(58) Field of Search .............................. 436/63, 164, 165, 436/174, 175, 52; 422/58, 73, 81, 82.05, 82.09, 102; 356/39, 317, 318, 335, 336, 337, 244, 246

(56) References Cited

U.S. PATENT DOCUMENTS

| | | |
|---|---|---|
| 3,565,286 | 2/1971 | Latham, Jr. . |
| 3,749,285 | 7/1973 | Latham, Jr. . |
| 4,212,742 | 7/1980 | Solomon et al. . |
| 4,482,342 | 11/1984 | Lueptow et al. . |
| 4,735,504 * | 4/1988 | Tycko ..................................... 356/336 |
| 5,633,167 * | 5/1997 | Fan et al. ................................ 436/17 |
| 5,656,154 | 8/1997 | Meryman . |
| 5,770,069 | 6/1998 | Meryman . |
| 5,983,120 * | 11/1999 | Groner et al. ........................ 600/310 |
| 6,067,158 * | 5/2000 | Itose et al. ............................ 356/340 |

* cited by examiner

Primary Examiner—Maureen M. Wallenhorst
(74) Attorney, Agent, or Firm—Harvey Fendelman; Peter A. Lipovsky; Michael A. Kagan

(57) ABSTRACT

A system for controlling the deglycerolization of red blood cells includes a cell sorter having multiple fluid channels each having a unique cross-sectional area for directing a fluid mixture consisting essentially of a saline solution and a plasma solution having glycerized red blood cell products through one or more of the fluid channels based on the sizes of the red blood cell products. An optical energy source illuminates the fluid mixture in the cell sorter, whereupon an optical detector generates a data signal in response to receiving light signals that propagate through the fluid mixture. A processor generates a control signal in response to receiving the data signal that is used by a servo-controlled device to control the ratio of the saline and plasma solutions in the fluid mixture so that the red blood cell products substantially flow only through one or more of the fluid channels having particular cross-sectional areas.

15 Claims, 4 Drawing Sheets

SYSTEM FOR CONTROLLING DEGLYCEROLIZATION OF RED BLOOD CELLS

BACKGROUND OF THE INVENTION

The present invention generally relates to the deglycerolization of blood, and more particularly, to a system which controls the deglycerolization of blood by monitoring the segregation of erythrocytes by size.

The Armed Services Blood Program Office (ASBPO) has established a policy of maintaining pre-positioned stockpiles of frozen red blood cells, and utilizing these stockpiles in times of conflict for U.S. combat casualties. In order to implement this policy, glycerol is allowed to be absorbed by red blood cells, which then are frozen and stored. The glycerol prevents damage to the erythrocytes. Presently, the only method approved by the Food and Drug Administration (FDA) for processing thawed-frozen red blood cells uses an open, nonsterile wash system that is manually monitored and operated. This system generally requires about 1½ to 2 hours to thaw and deglycerolize red blood cells from a cryogenic state. Because this system is not sterile, the FDA mandates that thawed-frozen red blood cells processed this way must be transfused within 24 hours or discarded. However, the time restrictions and requirement to discard the blood are not compatible with the logistics of the ASBPO policy. Therefore, a need exist for a sterile, automated method for monitoring and controlling the deglycerolization of thawed red blood cells in a more timely manner compared to the processing time of the standard method.

SUMMARY OF THE INVENTION

The present invention provides a system and method for controlling the deglycerolization of red blood cells. A system for controlling the deglycerolization of red blood cells includes a cell sorter having multiple fluid channels each having a unique cross-sectional area for directing a fluid mixture consisting essentially of a saline solution and a plasma solution having glycerized red blood cell products through one or more of the fluid channels based on the sizes of the red blood cell products. An optical energy source illuminates the fluid mixture in the cell sorter, whereupon an optical detector generates a data signal in response to receiving light signals that propagate through the fluid mixture. A processor generates a control signal in response to receiving the data signal that is used by a servo-controlled device to control the ratio of the saline and plasma solutions in the fluid mixture so that the red blood cell products substantially flow only through one or more of the fluid channels having particular cross-sectional areas.

These and other advantages of the invention will become more apparent upon review of the accompanying drawings and specification, including the claims.

BRIEF DESCRIPTION OF THE DRAWINGS

Throughout the several view, like elements are referenced using like references.

DESCRIPTION OF THE PREFERRED EMBODIMENT

Figure 1:
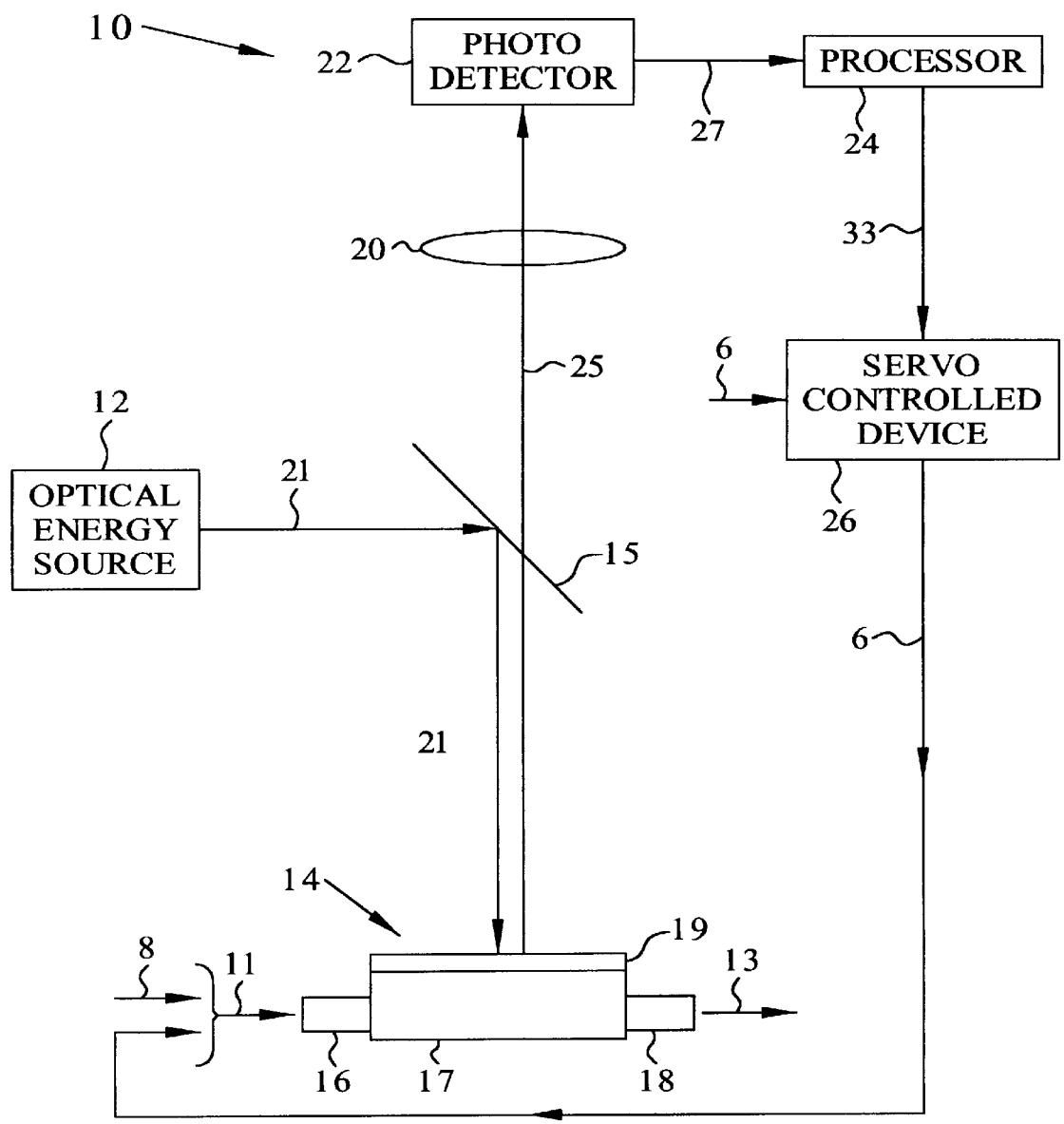
FIG. 1 illustrates a block diagram of a system for controlling deglycerolization of red blood cells embodying various features of the present invention.

Referring to FIG. 1, the present invention is directed to a system 10 for controlling deglycerolization of red blood cells. System 10 includes an optical energy source 12, cell sorter 14, optical element 15, lens 20, photo detector 22, processor 24, and servo-controlled device 26. In the operation of system 10, input fluid 11 enters fluid inlet 16 of cell sorter 14 and is deglycerolized as described further herein. Input fluid 11 generally consists of two components: 1) a solution 8 consisting essentially of glycerolized blood cells suspended in plasma; and 2) a saline solution 6. Generally deglycerolized output fluid 13, containing blood and glycerol products, exits cell sorter 14 through fluid outlet 18. Optical energy source 12 generates an optical beam 21 that is directed to cell sorter 14 by optical element 15. In the preferred embodiment, optical beam 21 is both polarized and quasi-monochromatic light. Polarized light enhances the contrast between the plasma and surrounding structures. Quasi-monochromatic light greatly reduces or eliminates chromatic aberration that could cause false indications of cell sizes. Quasi-monochromatic light has frequency components strongly peaked about a certain frequency. Examples of optical energy sources which generate quasi-monochromatic light suit suitable for use as optical energy source 12 include solid-state lasers, gas type lasers (such as an He—Ne laser), laser diodes, and light emitting diodes.

Optical beam 21 interrogates the contents of cell sorter 14 and is transformed into reflective optical signal 25 through interaction with fluid that transitions from solution 11 to solution 13 in the cell sorter. The characteristics of signal 25 represent the sizes of red blood cells in cell sorter 14. Next, optical signal 25 propagates through transparent window 19 and optical element 15, and then is focused by lens 20 onto photo detector 22. By way of example, optical element 15 may be a partially reflective mirror or a prism. Photodetector 22 transforms optical signal 25 into an electrical output signal 27 representing the sizes of the red blood cells in cell sorter 14. Photo detector 22 may be implemented as a charge coupled device, photo transistor array, vidicon, or any other type of device that provides sufficient pixel resolution of the field of view of the cell sorter.

The exposure of solution 8, containing glycerolized red blood cells, to saline solution 6, causes glycerol to be expelled through the walls of red blood cells (erythrocytes) at a rate determined by the osmotic pressure difference between the interior of the red blood cells and that of saline solution 6. Control of the osmotic pressure difference is very important because if the pressure gradient is too great, red blood cells will rupture. If the osmotic pressure difference is too small, the rate at which glycerol is expelled through the wall of the red blood cells will be very slow. The osmotic pressure difference increases as the ratio of the volume of solution 6 to solution 8 increases in fluid 11.

Processor 24 employs signal 27 to generate a control signal 33 that is used to supervise servo-controlled device 26. Control signal 33 has characteristics functionally related to the sizes of red blood cells found in cell sorter 14 within the field of view of photo detector 22. Servo-controlled device 26 is used to establish the ratio of saline solution 6 to the glycerolized red blood cells in solution 8 in input solution 11 in response to the sizes of red blood cells found in cell sorter 14 which are encoded in signal 25. Servo-controlled device 26 may, for example, be a pump or valve. Regulation of the ratio of solution 6 to solution 8 is used to optimize the rate at which glycerol is expelled from the red blood cells, an important goal of system 10.

Figure 2:
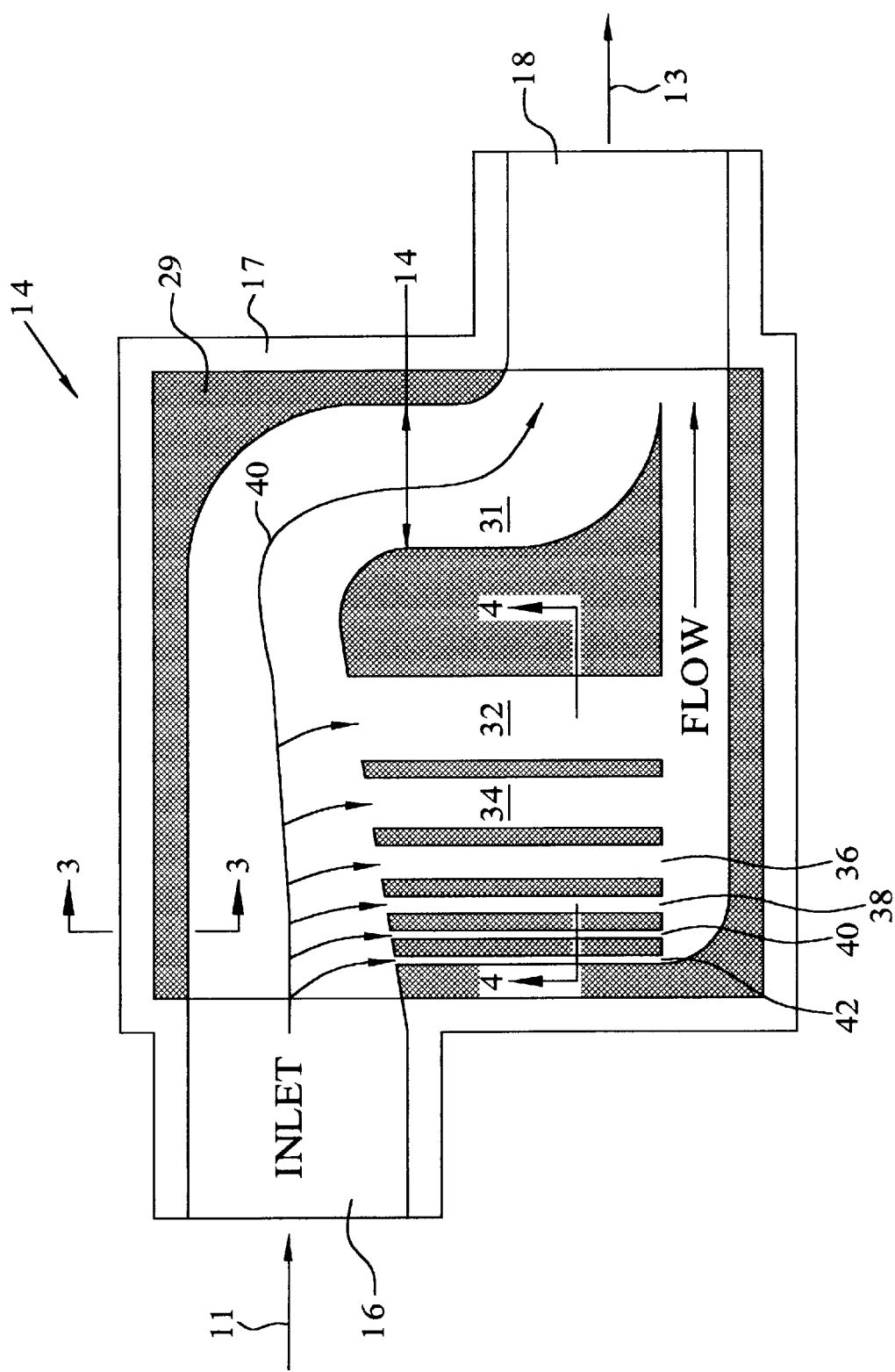
FIG. 2 illustrates a plan view of the cell sorter.
Figure 3:
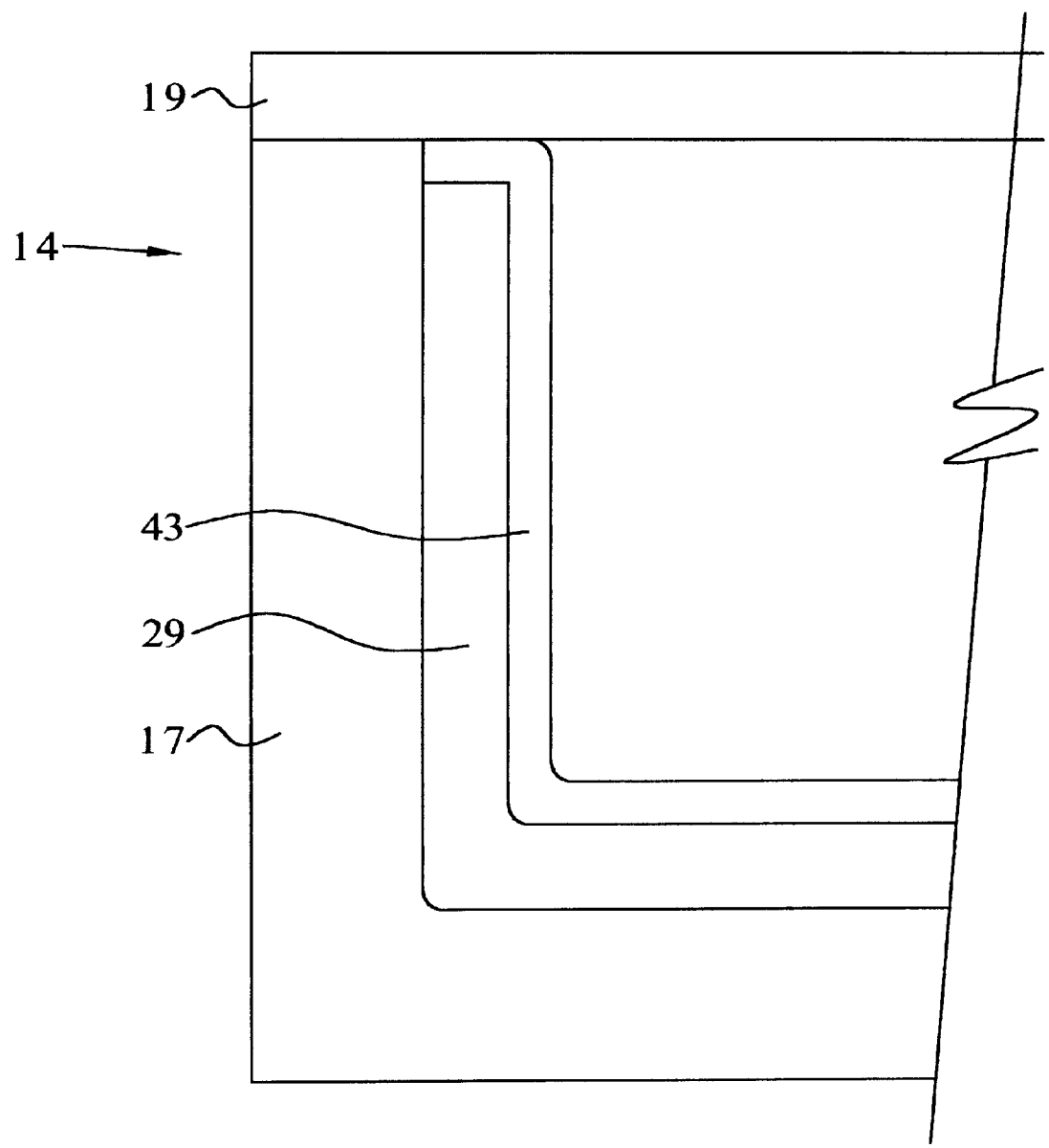
FIG. 3 is a view of the cell sorter taken along section 3—3 of FIG. 2.
Figure 4:
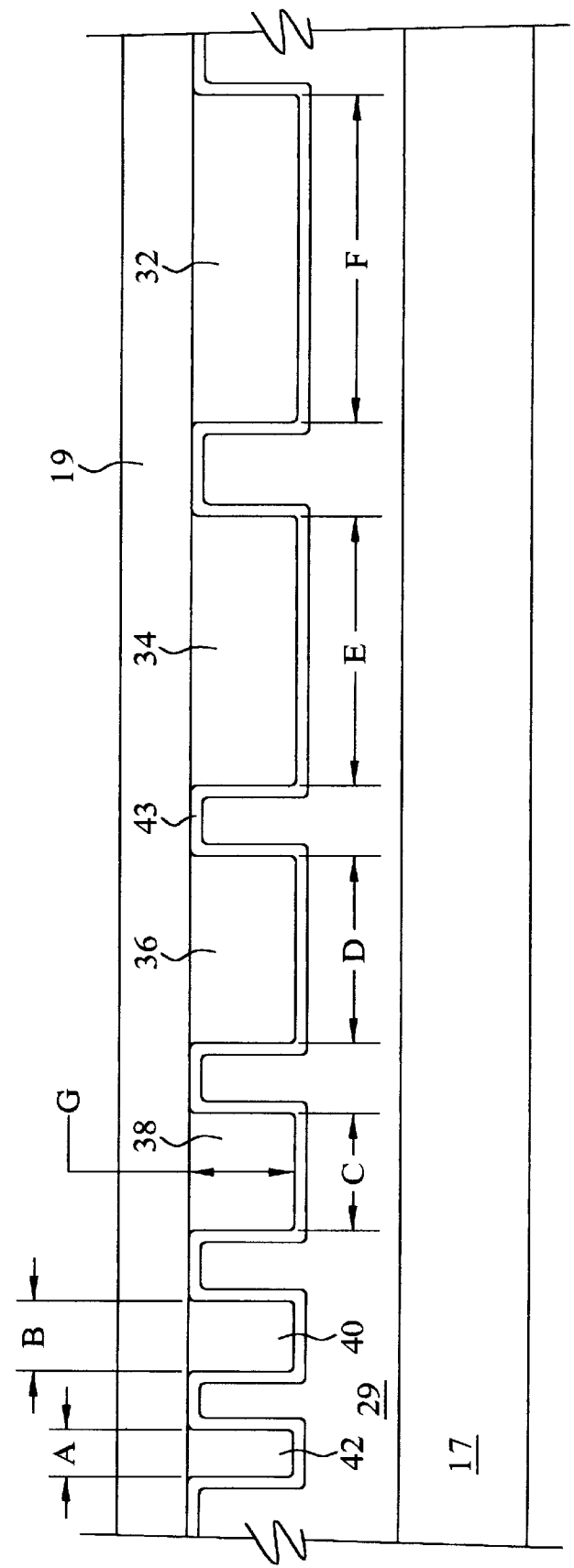
FIG. 4 is a view of the cell sorter taken along section 4—4 of FIG. 2.

As described with reference to FIGS. 2 and 3, cell sorter 14 includes an external body 17 on which an optically transparent window 19 is attached so as to create a water tight, or more generally, fluid tight seal. External window 19 may be made from materials such as glass, quartz, polycarbonate, sapphire or of any other type of optically transparent material that is essentially chemically inert to blood components and chemicals to which the window is be exposed, and which may be sterilized. External body 17 also supports a flow divider insert 29 having multiple flow dividing channels for input fluid 11 into several flow streams having different cross-sectional areas. By way of example, insert 29 is shown to include seven fluid flow dividing channels 31, 32, 34, 36, 38, 40, and 42, each of which are in fluid communication with inlet 16 and outlet 18 of cell sorter 14. After entering inlet 16, input fluid 11 is divided into separate fluid streams by channels 31, 32, 34, 36, 38, 40, and 42. The separate fluid streams then merge before exiting cell sorter 14 through outlet 18. Although the invention has been described as having seven flow channels, the scope of the invention includes the use of any number of flow channels required to suit the requirements of a particular application. Each flow channel preferably has a unique cross-sectional area in a plane orthogonal to the direction of fluid flow. FIG. 4 shows a cross-sectional view of channels 31, 32, 34, 36, 38, 40, and 42. Exemplary dimensions for the channels are provided in TABLE 1 below. Insert 29 may be fabricated from bulk silicon using standard photolithographic techniques. A layer 43 supported by and attached to insert 29 generally consists of a material that should be essentially chemically resistant to blood components and which may be sterilized. Layer 43 should be optically reflective in the regions of cell sorter 14 through which fluid containing blood products flows. Examples of reflective materials suitable for layer 43 include gold, nickel, passivated aluminum, and silicon dioxide ($SiO_2$). Reflective layer 43 caused incoming light beam 21 to be reflected out of cell sorter 14 as light signal 25. A further requirement of cell sorter 14 is that it be made of materials that can be sterilized. Techniques for sterilizing cell sorter 14 may include exposure to gamma radiation or heat.

TABLE 1

| Channel | Width ($\mu$) | Height ($\mu$) |
|---------|---------------|----------------|
| 31 | H ≈ 3 mm | G ≈ 1.4–1.6 |
| 32 | F ≈ 18–22 | G ≈ 1.4–1.6 |
| 34 | E ≈ 12–15 | G ≈ 1.4–1.6 |
| 36 | D ≈ 8–9 | G ≈ 1.4–1.6 |
| 38 | C ≈ 5–7 | G ≈ 1.4–1.6 |
| 40 | B ≈ 2–3 | G ≈ 1.4–1.6 |
| 42 | A < 2 | G ≈ 1.4–1.6 |

Saline causes glycerolized red blood cells to expel the glycerol due to the osmotic pressure difference between glycerol and saline. If the osmotic pressure is too much, i.e., when the ratio of saline to glycerolized red blood cells in input solution 11 exceeds some level, the red blood cells rupture, a process referred to as hemolysis. If the red blood cells rupture, then fragments of red blood cells having some linear dimensions of about 2–3$\mu$ would find their way into channel 40. Red blood cells, however, are too small to enter channel 40. This may be referenced as a case 1 situation. A case 1 situation means that the ratio of saline solution 6 to solution 8 is too high. In such case, processor 24 generates signal 24 whereby servo-controlled device 26 reduces the ratio of solution 6 to solution 8 in solution 11. Plasma may enter channel 42. However, red blood cell fragments are too large to enter channel 42. Therefore, the optical detection of plasma in channel 42 may be used as a reference to normalize reflected light signal 25 due to variations in the optical transparency characteristics of the plasma.

At the opposite extreme of case 1 is the case 2 situation where unconfined red blood cells swollen with glycerol have minimum linear dimensions of about 15–16$\mu$. Cells of this size will not be able to enter any of channels 32, 34, 36, 38, and 40, but will be able to pass through channel 31. A case 2 situation means that the glycerol is not being emitted from the cells. Therefore, processor 24 generates signal 33 that directs servo-controlled device 26 to respond so that the ratio of saline solution 6 to solution 8 of glycerolized red blood cells is increased by some predetermined increment. As the ratio is increased the red blood cells will emit more glycerol and become smaller.

In the preferred operation of system 10, deglycerolized red blood cells progressively find their way into increasingly smaller channels 34, 36, and 38 as characteristics of signal 33 are changed so that servo-controlled device 26 effectuates an optimum ratio of saline solution 6 to glycerolized blood solution 8. Under ideal operating conditions, red blood cells are found in channel 38, but essentially no red blood cell fragments are found in channel 40. Such a condition indicates that practically all of the glycerol has been expelled from the red blood cells, but the cells have not fragmented due to hemolysis. Therefore, the cross-sectional area of channel 38 is sized so that unconfined red blood cells which are engorged with glycerol are able to pass through. However, channel 40 is sized so that nothing larger than blood cell fragments may transit. Thus, channel 40 has insufficient area to admit red blood cells that are not engorged with glycerol. Channel 42 is sized to admit plasma, but has too small a cross-sectional area to admit red blood cell fragments or anything larger. Channels 34 and 36 are sized to have progressively smaller cross-sectional areas that admit red blood cells which are decreasingly engorged with glycerol to facilitate monitoring the process of expelling glycerol from the cells.

Characteristics of signal 33 that may be used to control a servo-controlled mechanism such as device 26 include pulse width, amplitude, frequency, logic level, and any other type of signal characteristic that may be used to control a servo-controlled device. Thus, it may be appreciated that the present invention provides an automated system for monitoring and controlling the deglycerolization of red blood cells in real time so that the cells expel glycerol at a timely rate without causing, or at least minimizing hemolysis.

Obviously, many modifications and variations of the present invention are possible in light of the above teachings. It is therefore to be understood that within the scope of the appended claims, the invention may be practiced otherwise than as specifically described.

What is claimed is:

1. A system for controlling the deglycerolization of red blood cells, comprising:

a cell sorter having multiple fluid channels each having a unique cross-sectional area for directing a fluid mixture consisting essentially of a saline solution and a plasma solution having glycerized red blood cell products through one or more of said fluid channels based on the sizes of said red blood cell products;

an optical energy source for illuminating said fluid mixture in said cell sorter;

an optical detector for generating a data signal in response to receiving light signals that propagate through said fluid mixture;

a processor for generating a control signal in response to receiving said data signal; and a servo-controlled device for controlling the deglycerolization of said red blood cell products by controlling a ratio of said saline and plasma solutions in said fluid mixture under the supervision of said control signal so that said red blood cell products substantially flow only through one or more of said fluid channels having particular cross-sectional areas.

2. The system of claim 1 wherein said cell sorter has an optically reflective layer.

3. The system of claim 2 wherein said optically reflective layer is essentially chemically inert to blood components.

4. The system of claim 3 wherein said optically reflective layer is selected from the group consisting of gold, nickel, silicon dioxide, and passivated aluminum.

5. The system of claim 1 wherein said control signal has properties monotonically related to said sizes of said red blood cell products.

6. The system of claim 1 wherein said control signal has properties related to said sizes of said red blood cell products by a monotonically decreasing function.

7. The system of claim 1 wherein said control signal has properties related to said sizes of said red blood cell products by a monotonically increasing function.

8. The system of claim 1 wherein said optical detector is selected from the group consisting of a charge coupled device, phototransistor array, and vidicom.

9. The system of claim 1 wherein said cell sorter includes an optically transparent cover mounted over said fluid channels.

10. The system of claim 9 wherein said optically transparent cover consists essentially of a material selected from the group consisting of glass, quartz, sapphire, and polycarbonate.

11. The system of claim 1 wherein said optical energy source illuminates said fluid mixture with a polarized light signal.

12. The system of claim 1 wherein said optical energy source illuminates said fluid mixture with a quasi-monochromatic light signal.

13. A method for controlling the deglycerolization of red blood cells, comprising the steps of:

forming a fluid mixture that includes a saline solution and a plasma solution having glycerolized red blood cell products;

directing said fluid mixture through multiple fluid channels each having a different cross-sectional area;

directing a light beam through said fluid mixture in each of said fluid channels;

generating a data signal in response to detecting said light beam after said light beam passes through said fluid mixture;

generating a control signal in response to receiving said data signal;

using said control signal for controlling the deglycerolization of said red blood cell products by controlling a ratio of said saline solution to said plasma solution in said fluid mixture so that said red blood cell products substantially flow only through one or more of said fluid channels having particular cross-sectional areas.

14. The method of claim 13 wherein said light beam is polarized.

15. The method of claim 13 wherein said light beam is quasi-monochromatic.

* * * * *